(12) United States Patent
Blomet et al.

(10) Patent No.: US 11,197,874 B2
(45) Date of Patent: *Dec. 14, 2021

(54) USE OF AN AMPHOTERIC CHELATING AGENT FOR PREVENTING CONTACT ALLERGIES

(71) Applicant: PREVOR INTERNATIONAL, Paris (FR)

(72) Inventors: Joel Blomet, Valmondois (FR); Laurence Mathieu, Talence (FR); Marie-Claude Meyer, Paris (FR)

(73) Assignee: PREVOR INTERNATIONAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/415,146

(22) PCT Filed: Jul. 17, 2013

(86) PCT No.: PCT/FR2013/051718
§ 371 (c)(1),
(2) Date: Jan. 16, 2015

(87) PCT Pub. No.: WO2014/013195
PCT Pub. Date: Jan. 23, 2014

(65) Prior Publication Data
US 2015/0202217 A1 Jul. 23, 2015

(30) Foreign Application Priority Data
Jul. 18, 2012 (FR) .................................. 12 56939

(51) Int. Cl.
| | | |
|---|---|---|
| A61K 31/69 | (2006.01) | |
| A61K 9/00 | (2006.01) | |
| A61K 47/18 | (2017.01) | |
| A61K 47/20 | (2006.01) | |
| A61K 31/198 | (2006.01) | |
| A61Q 17/00 | (2006.01) | |
| A61K 31/197 | (2006.01) | |

(52) U.S. Cl.
CPC ............ *A61K 31/69* (2013.01); *A61K 9/0014* (2013.01); *A61K 31/197* (2013.01); *A61K 31/198* (2013.01); *A61K 47/183* (2013.01); *A61K 47/20* (2013.01); *A61Q 17/00* (2013.01); *A61K 2800/51* (2013.01)

(58) Field of Classification Search
CPC ...... A61K 31/69; A61K 47/20; A61K 47/183; A61K 31/197; A61K 31/198; A61K 9/0014; A61K 2800/51; A61Q 17/00; A61P 37/08; A61P 17/16; A61P 17/00
See application file for complete search history.

(56) References Cited

U.S. PATENT DOCUMENTS

| | | | | |
|---|---|---|---|---|
| 5,091,171 A | * | 2/1992 | Yu ............................. | A61K 8/26 424/642 |
| 5,665,804 A | * | 9/1997 | Hill ........................ | A61K 8/585 424/401 |
| 5,763,486 A | | 6/1998 | Blomet et al. | |
| 6,706,313 B1 | * | 3/2004 | Goldstein et al. ............. | 427/2.3 |
| 2009/0192244 A1 | * | 7/2009 | Doyle et al. .................... | 524/17 |
| 2012/0321573 A1 | * | 12/2012 | Karp .................... | A61K 9/0014 424/59 |

FOREIGN PATENT DOCUMENTS

WO 01/93858 A2 12/2001

OTHER PUBLICATIONS

Google machine translation of WO 2001/093858 A2; original document published Dec. 13, 2001, p. 1-4.*
Mayo Clinc Staff, "Diseases and Conditions: Asthma," <http://www.mayoclinic.org/diseases-conditions/asthma/basics/prevention/con-20026992>, Mayo Clinic, © 1998-2015 Mayo Foundation for Medical Education and Research, p. 1-8.*
A. Morris, "Wasp and Insect Allergy," Dr. Adrian Morris Surrey Allergy Clinic, London, <http://www.allergyclinic.co.uk/moreaboutallergy/waspallergy>, published Jan. 6, 2012, p. 1-5.*
Tammaro et al., "Topical and Systemic Therapies for Nickel Allergy," Dermatitis. 2011; 22(05):251-255.*
Dr. Adrian Morris, "Wasp and Insect Allergy," <http://www.allergyclinic.co.uk/moreaboutallergy/waspallergy>, published Jan. 6, 2012, p. 1-5.*
International Search Report, dated Aug. 30, 2013, from corresponding PCT application.
"Chemical Analysis", edited mainly by Liu Zhen, Chemical Industry Press, the first edition, the first print on Sep. 1983, pp. 251-253 (5 pp., including machine-generated English Abstract).
Rui Shi et al. "Allergy and Treatment", China Science and Technology Press, the first edition, the first print on Jul. 2008, pp. 1-3 (6 pp., including partial machine-generated English translation).

* cited by examiner

*Primary Examiner* — Nannette Holloman
(74) *Attorney, Agent, or Firm* — Maier & Maier, PLLC

(57) ABSTRACT

A method of preventing contact allergies includes using at least one amphoteric chelating agent which includes a complex based on aluminium and on ethylenediaminetetraacetic acid or the trisodium salt thereof, having the general formula [Al(Y)Bn]c'Dc with B being $OH^-$, $BO_2^-$ or $H^+$, Y being a tetracarboxylate which can be protonated four times to form ethylenediaminetetraacetic acid, n being an integer equal to 0, 1, 2 or 3, D being a counterion, preferably $Na^+$, c being an integer equal to 0, 1, 2 or 3 and c' being a relative number having the same absolute value as c. A device, a part of which includes the amphoteric chelating agent, is also described.

22 Claims, 1 Drawing Sheet

USE OF AN AMPHOTERIC CHELATING AGENT FOR PREVENTING CONTACT ALLERGIES

FIELD OF THE INVENTION

The present invention relates to the field of products for preventing contact allergies.

CONTEXT OF THE INVENTION

Contact allergies, and in particular allergy due to contact with objects or devices made of rubber, have greatly increased over the past few years. Although they are normally moderate, the symptoms may in certain cases have serious consequences. Allergies can in fact be of two types:
  immediate with urticaria, rhinitis, conjunctivitis, asthma and a risk of anaphylaxis (state of shock and/or asphyxia);
  delayed with allergic contact dermatitis (eczema).

Contact allergies develop through repeated contact with allergenic substances.

Allergy to rubber, and in particular to latex, more particularly to natural latex, affects 1% to 5% of the population. It affects more particularly individuals exposed to repeated contact with rubber, such as individuals working in the medical sector. Thus, 5% to 22% of medical personnel, nurses, doctors, surgeons, physiotherapists, podiatrists, develop allergies to rubber. Patients who have undergone numerous operations are also liable to develop allergies to latex, as are individuals working in laboratories or hairdressing salons who use rubber gloves, individual who use prophylactic methods involving condoms and individuals who work in the rubber industry.

Allergy to rubber represents the $2^{nd}$ most common cause of anaphylactic shock during anesthesia. Allergy to natural rubber (LN) has been recognized as a public health problem since the end of the 1980s.

Natural rubber or latex is an aqueous emulsion of spherical droplets of polyisoprene which are covered with a layer of water-soluble proteins. It may be of synthetic or natural origin. In natural form, it comes from the sap of *Hevea brasiliensis*. It is highly present in the objects of daily life. By way of examples of objects made of latex or comprising latex which are therefore capable of causing allergic reactions, mention may be made of household gloves, tires, balloons, pacifiers, snorkels, flippers, swimming goggles, bath caps, adhesives, tennis racket grips, condoms, medical material: elastic bandages, syringes with rubber seals, catheters, undersheets, perfusion tubing, mouthpieces for dental care and examination gloves or surgical gloves, etc.

The best way to prevent contact allergies is to avoid the use and/or contact with objects containing allergenic substances. Thus, in order to prevent allergies to rubber, it is recommended not to use objects made of rubber.

Replacement products exist, in particular made of polyurethane, polyvinyl, nitrile, etc., making it possible to replace the objects or devices made of rubber, but they prove to be much more expensive and, as regards finger stalls, gloves and condoms, they affect touch sensitivity. There is therefore a real need for a product which makes it possible to prevent contact allergies and in particular allergies to rubber.

Surprisingly and unexpectedly, the present inventors have found that a particular amphoteric chelating agent makes it possible to prevent contact allergies.

SUMMARY OF THE INVENTION

Generally, the present invention relates to the use of at least one amphoteric chelating agent which comprises a complex based on aluminum and on ethylenediaminetetraacetic acid or the trisodium salt thereof, having the general formula $[Al(Y)B_n]^c D_c$ with B being $OH^-$, $BO_2^-$ or Y being a tetracarboxylate which can be protonated four times so as to form ethylenediaminetetraacetic acid, n being an integer equal to 0, 1, 2 or 3, D being a counterion, preferably $Na^+$, c being an integer equal to 0, 1, 2 or 3 and c' being a relative number having the same absolute value as c, for preventing contact allergies.

According to another aspect, the present invention relates to a device comprising a part made of allergenic material, in particular made of latex, intended to come into contact with the skin or the mucous membranes, which is covered with a layer containing at least one amphoteric chelating agent as mentioned above.

According to yet another subject, the present invention relates to the use of a composition comprising at least said amphoteric chelating agent mentioned above and at least one excipient, for preventing contact allergies.

DETAILED DESCRIPTION OF THE INVENTION

Figure 1:
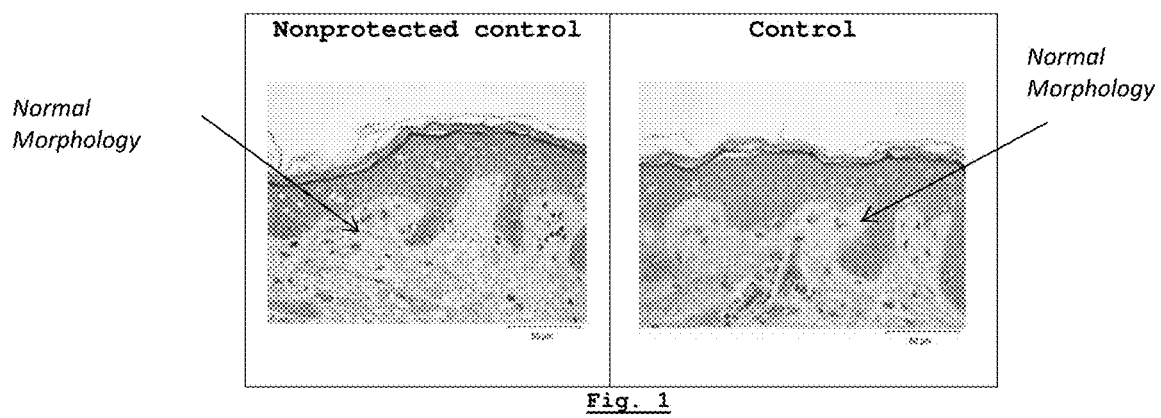
FIG. 1 is a photograph by Scanning Electron Microscopy of the explants of Example 4 at T0.

The present invention relates to the use of at least one amphoteric chelating agent which comprises a complex based on aluminum and on ethylenediaminetetraacetic acid or the trisodium salt thereof, having the general formula $[Al(Y)B_n]^c D_c$ with B being $OH^-$, $BO_2^-$ or Y being a tetracarboxylate which can be protonated four times so as to form ethylenediaminetetraacetic acid, n being an integer equal to 0, 1, 2 or 3, D being a counterion, preferably $Na^+$, c being an integer equal to 0, 1, 2 or 3 and c' being a relative number having the same absolute value as c, for preventing contact allergies, in particular allergies to rubber.

In the present invention, the term "contact allergies" is intended to mean all the allergies which are caused by repeated contact of allergenic substances with the skin and/or the mucous membranes. By way of allergens present in objects or devices liable to come into contact with the skin and/or the mucous membranes and which cause contact allergies, mention may be made of latex proteins, heavy metals such as Al, As, Cd, Cr, Hg, Ni, Pb, Sr and Te, tetramethylthiuram disulfide, 2-mercaptobenzothiazole, benzyl carbamate, bisphenol, ethyl acrylate, araldite 506 epoxy resin, methanal, protein-type allergens (such as profilins, tropomyosins, LTPs (lipid transfer proteins), PR-10 bet V1-like proteins, polcalcins, beta-parvalbumins, 2s albumins, beta-expansins, polygalacturonases, Ag5 (antigens 5), albumins, caseins, lipocalins, grass group 5 allergens, 11s globulins, 7s vicilin-like globulins, grass group 4 allergens, papain-like cysteine proteases, phospholipases A1, serine protease inhibitors, hyaluronidases, class 1 chitinases, thaumatin-like proteins, etc.) and mixtures thereof.

The invention is particularly suitable for the prevention of allergies to rubber, and in particular to natural rubber. In the present invention, the term "allergies to rubber" is intended to mean the allergies caused by the proteins present in natural rubber derived from the *Hevea brasiliensis* tree, but also by other allergenic substances present in rubber. By way of examples of such allergenic proteins, mention may be made of hevein, prohevein, profilin, rubber elongation factor, endo-1,3-β-glucosidase, etc. Other examples of non-protein allergenic substances present in rubber are vulcanizing agents (thiurams, dithiocarbamates, benzothiazoles, guanidines and thioureas), antioxidants or antiozonants (derived from PPD—para-phenylenediamine—and quinolines), phenols (hydroquinones), phosphites, etc., or other additives, such as chlorhexidine digluconate, dimethyldidecylammonium chloride salts, isothiazolinones, formaldehyde, various metals, etc.

Such contact allergies manifest themselves through contact dermatitis, contact urticaria, eczema, rhinitis, conjunctivitis, asthma and anaphylactic shock.

In the text of the present application, the term "contact allergies" or "allergies to rubber" will denote without distinction the allergy and the manifestations thereof.

The amphoteric chelating agent of general formula $[Al(Y)B_n]^{c'}D_c$ used according to the invention can preferably be formed by a virtually stoichiometric combination of the aluminum ion $Al^{3+}$, of the ligand Y and of a stabilizing agent chosen from $OH^-$, $BO_2^-$ or $H^+$. Consequently, its pH remains neutral, the smallest of its acid pK values is in the range from 6 to 10, while the largest of its basic pK values is in the range from 5 to 8, and the largest basic pK is lower than the smallest acid pK.

According to one particular embodiment, said complex based on aluminum and on Y is stabilized by a weak base such as the amino acids chosen from the group comprising glycine, histidine, arginine, lysine, phenylalanine, alanine, isoleucine, leucine, methionine, proline, valine, tryptophan, serine, glutamine, cystine, and mixtures thereof. Glycine is entirely appropriate.

According to the invention, the use of said amphoteric chelating agent is carried out in such a way that it is in contact with the skin and/or the mucous membranes.

The effectiveness of the use of the amphoteric chelating agent in accordance with the invention has been tested using morphological analyses based on the following theory: Langerhans cells are dendritic cells which are found in the epidermis which contain Birbeck granules. They normally exist in lymph nodes and in the skin at the level of the stratum spinosum of the epidermis. These cells which specialize in antigen uptake become activated when the skin is brought into contact with an allergen. This provides a first sign of the beginning of a sensitization process. Methods of immunolabeling, in particular of CD1a surface receptors of Langerhans cells, make it possible to measure the number thereof and to observe their migration from the epidermis to the dermis. The preventive composition of the invention is effective if the antigen is stopped, i.e. not taken up by the epidermal Langerhans cells. Said cells will not therefore migrate to the dermis. The effectiveness of the composition according to the invention is therefore measured by the number of non-migrating Langerhans cells per centimeter of epidermis. No substantial migration of the number of these cells was observed after bringing the area of skin covered with the composition according to the invention into contact with allergenic agents and in particular with the allergenic proteins of natural rubber, such as hevein.

The invention also relates to a device comprising a part made of material which may contain allergens, intended to come into contact with the skin or the mucous membranes, which is covered with a layer containing at least one amphoteric chelating agent which comprises a complex based on aluminum and on ethylenediaminetetraacetic acid or the trisodium salt thereof, having the general formula $[Al(Y)B_n]^{c'}D_c$ with B being $OH^-$, $BO_2^-$ or $H^+$, Y being a tetracarboxylate which can be protonated four times so as to form ethylenediaminetetraacetic acid, n being an integer equal to 0, 1, 2 or 3, D being a counterion, preferably $Na^+$, c being an integer equal to 0, 1, 2 or 3 and c' being a relative number having the same absolute value as c.

The invention is particularly suitable for devices made of rubber or comprising a part made of rubber intended to come into contact with the skin and/or the mucous membranes.

Examples of a device according to the invention are condoms, gloves, finger stalls, bandage and compresses, medical devices such as catheters, tubing, draining devices, perfusion devices, medical devices of use in urology, medical devices for respiratory access, etc.

According to one particular embodiment, at least the part of the device intended to come into contact with the skin and/or the mucous membranes is covered with a film comprising said amphoteric chelating agent.

Said film is preferably a lubricating preparation.

In the case of condoms, both the external surface and the internal surface can be covered with a lubricating preparation comprising said amphoteric chelating agent so as to prevent both partners from having allergies to latex.

The invention also relates to the use of a composition comprising at least one amphoteric chelating agent which comprises a complex based on aluminum and on ethylenediaminetetraacetic acid or the trisodium salt thereof, having the general formula $[Al(Y)B_n]^{c'}D_c$ with B being $OH^-$, $BO_2^-$ or $H^+$, Y being a tetracarboxylate which can be protonated four times so as to form ethylenediaminetetraacetic acid, n being an integer equal to 0, 1, 2 or 3, D being a counterion, preferably $Na^+$, c being an integer equal to 0, 1, 2 or 3 and c' being a relative number having the same absolute value as c, and at least one excipient, for preventing contacting allergies and in particular allergies to rubber.

The composition may be in the form of an oil-in-water or water-in-oil emulsion, or in the form of a gel, in particular a hydrophilic gel or a silicone gel.

Said excipient present in the composition is an excipient of pharmaceutical or cosmetic quality.

Examples of excipients which may be present in the composition according to the invention are chosen from a gelling agent, surfactants, synthetic or natural waxes or oils, moisturizing agents and emollients, antiperspirants, texture-improving additives, such as conditioners and thickeners, preserving agents, cosmetic and food dyes, fragrances, flavorings, pH-regulating agents, and mixtures thereof.

The gelling agent or thickener may be hydrophilic or may be of silicone type. The hydrophilic gelling agents may be synthetic gelling agents, semi-synthetic gelling agents, or natural gelling agents of plant, microbial, animal or mineral origin. The hydrophilic gelling agents may, for example, be acrylic acid polymers and copolymers, $C_{10}$-$C_{30}$ alkyl acrylate/acrylate crosslinked polymers, polyacrylamide, poloxamer, cellulose-based derivatives (esters and ethers), silicas, fumed silica, silicates, such as magnesium aluminum silicates, chitin and derivatives thereof, gelatin, xanthan, dextran, gellan, carraghenans, alginates, agar-agar, agar, pectin, acacia gum, karaya gum, tragacanth, gum arabic, guar gum, locust bean gum, starch and derivatives thereof, or scleroglucan. The concentration of gelling agent or thickener is from 0.01% to 10% by weight, preferably from 0.1% to 5% by weight, and even more preferentially from 0.5% to 3% by weight of the total weight of the composition.

The gelling agent of silicone type is, for example, a polysiloxane.

The surfactant may be hydrophobic with an HLB of 3 to 10 or hydrophilic with an HLB of 11 to 18. This surfactant is chosen from the group comprising ethoxylated fatty alcohols, fatty acids and fatty esters (for example: ceteareth-12, ceteareth-20, ceteareth-33, 20-ethoxylated stearyl cetyl alcohol, polyglyceryl-2 polyhydroxystearate, glyceryl oleate, sorbitan ester, glycerol ester, PEG mono/di-laurate, PEG mono/di-stearate, cetearyl isononanoate, glyceryl stearate, etc.), carboxylates, ethoxycarboxylates (for example: sodium/potassium stearate, alkyl-carboxylic acid, alkyl polyglycol ether carboxylic acid, alkylphenol polyglycol ether carboxylic acid, carboxymethyl alcohol, ethoxycarboxylate, ether carboxylate, etc.), and mixtures thereof. The amount of surfactant, when it is present, is from 0.1% to 10% by weight, preferably from 0.5% to 5% by weight, and even more preferentially from 1% to 3% by weight of the total weight of the composition.

The synthetic or natural waxes or oils are chosen from the group comprising carnauba extract, beeswax, Shea butter, triglycerides, stearins, esters of fatty acids (for example: cetearyl alcohols, dicaprylyl ethers of cetyl palmitate, dicaprylyl carbonates, cetearyl isononanates, distearyl-tricarbonate dimers, etc.), silicone oils, zinc stearates, polyisobutenes, octyldodecanols, octyldecyl xylosides, fatty alcohols, fatty acids (for example: lauric acid, myristic acid, stearic acid, etc.), plant oils (for example: sunflower oil, jojoba oil, *Cocos nucifera* oil, soybean oil, almond oil, etc.), vaseline, lanolin and mixtures thereof.

The moisturizing agents and emollients can be chosen from the group comprising allantoin, polyol (for example, glycerol, glycerol polymers, propylene glycol, sorbitol etc.), plant extracts (for example extracts of aloe vera, of chamomile, of cucumber, of calendula, etc.), hyaluronic acid, pyrrolidonecarboxylic acid, urea, chitosan, tocopherol, panthenol, butylene glycol, phospholipid, linoleic acid, γ-linoleic acid, alpha-bisabolol, and mixtures thereof.

The concentration of moisturizing agents and emollients is from 0.1% to 20% by weight, preferably from 0.5% to 10% by weight, and even more preferentially from 1% to 5% by weight of the total weight of the composition.

The antiperspirants can be chosen from the group comprising aluminum salts, preferably aluminum sesquihydrochloride, salts of aluminum and zirconium, aluminum zirconium octachlorohydrex glycine complexes, and mixtures thereof. The concentration of antiperspirant is from 0.1% to 50% by weight, preferably from 10% to 30% by weight, and even more preferentially 15% by weight of the total weight of the composition.

The conditioners can be chosen from the group comprising polycationic polymers denoted according to the INCI nomenclature as polyquaterniums, quaternized gums, quaternized phospholipids, and mixtures thereof. The concentration of conditioner is from 0.1% to 20% by weight, preferably from 0.5% to 10% by weight, and even more preferentially from 0.5% to 5% by weight of the total weight of the composition.

The preservatives can be chosen from the group comprising: para-hydroxybenzoic alkyl ester, isothiazolinone, imidazolidinyl urea, diazolidinyl urea, bromo-nitro-propanediol, phenoxyethanol, sorbic acid and salts thereof, benzoic acid and salts thereof, phenoxyethanol, benzyl alcohol, and mixtures thereof. The concentration is that authorized in cosmetics.

The concentration of cosmetic and food dyes, fragrances, flavorings, pH-regulating agents (for example, citric acid, lactic acid, phosphoric acid, sodium hydroxide, potassium hydroxide, aminomethylpropanol, triethanolamine, etc.), and mixtures thereof, is from 0.1% to 50% by weight, preferably from 10% to 30% by weight, and even more preferentially 15% by weight of the total weight of the composition.

Particularly advantageously, the composition is a gelling preparation, in particular a lubricating preparation.

The lubricating preparation is a hydrophilic preparation, a silicone preparation or a vaseline-based lubricating preparation containing said amphoteric chelating agent, either in liquid form or in solid form.

The amount of amphoteric chelating agent present in said composition is from 0.01% to 5%, preferably from 0.02% to 4.4% and even more preferentially about 2% by weight of the total weight of the composition. For certain applications, where the amounts of allergens are very low, in particular when deproteinated latex is used, very small amounts, even lower than 0.01%, might prove to be sufficient. However, in the majority of cases, an amount lower than 0.01% does not make it possible to obtain a sufficient preventive effect. No substantial improvement is observed above 5%.

According to the invention, the composition is used by topical application, more particularly topical application to the skin. It can also be used by application to the surface of the device intended to come into contact with the skin and/or the mucous membranes.

Without wishing to be bound by any theory, the present inventors are of the opinion that the composition according to the invention makes it possible to produce a physical and chemical barrier against the allergens. More particularly, after application and drying, a barrier layer covers the skin, thus providing a physical barrier between the skin and the external environment, the amphoteric chelating agent, for its part, providing a chemical barrier by chelating or chemically reacting with the allergens coming into contact with this composition.

By virtue of this double action, the allergens are prevented from coming into contact with the skin.

In order to be effective, the composition must completely cover the area of skin and/or of mucous membrane liable to come into contact with the latex device, generally the hands for latex gloves or the sex for condoms. It must be applied to the entire surface of contact. The amount of application of the composition according to the invention is in a proportion of about 0.5 to 5 mg/cm$^2$, preferably of about 1 to 3 mg/cm$^2$, and even more preferentially of about 1.5 mg/cm$^2$.

EXAMPLES

The following examples describe certain embodiments of the present invention. However, it is understood that the examples are presented only by way of illustration and do not in any way limit the scope of the invention.

In the present examples, the amphoteric chelating agent used has the following formula: $[AlYBO_2]^{2-}Na^+_2$.

Example 1: Lubricating Composition

A lubricating composition containing the following is prepared:

| | |
|---|---|
| *Aloe vera* | 0.1 mg |
| Vaseline | 100 mg |

-continued

| | |
|---|---|
| Lanolin | 35 mg |
| Water | 15 mg |
| Amphoteric chelating agent | 0.08 mg |

Example 2: Gel 49.5 ml of water
0.5 g of xanthan gum
0.2 mg of amphoteric chelating agent.

The gel is prepared in the following way: water is poured into a container. Stirring is carried out while adding the gum and the amphoteric chelating agent. The mixture is left to stand for 10 min.

Mixing is carried out in order to obtain a smooth texture.

Example 3: Emulsion for External Use

An emulsion comprising the following products was prepared.

| | |
|---|---|
| Glyceryl stearate/Cetearyl alcohol/cetyl palmitate/Coconut glycerides (weight ratio: 60%/20%/10%/10%) | 0.12 g |
| Ethoxylated cetearyl alcohol (12 mol) | 0.01 g |
| Ethoxylated cetearyl alcohol (20 mol) | 0.02 g |
| C18-caprylate/caprate | 0.09 g |
| Caprylic/capric triglyceride | 0.03 g |
| Liquid paraffin | 0.02 g |
| Propylparaben/benzoate paraben (50/50 w/w) | 0.004 g |
| Purified water | qs 1 g |
| Glycerol | 0.03 g |
| Amphoteric chelating agent | 0.002 g |

This oil-in-water emulsion has the following characteristics:
Brookfield viscosity of 18 000 cP, measured at a temperature of 20(+/−1°) C. with a spindle speed at 3/20 rpm (0.94 rad/min),
pH of 6.45,
no phase separation occurred after storage for 6 months at ambient temperature.

Example 4: Test for Effectiveness Against Allergens

Skin explants with an average diameter of 10 mm, originating from an abdominoplasty on a 49-year-old caucasian woman, are prepared. These explants are kept alive in a BEM culture medium (BIO-EC explant medium) at 37° C. in a humid atmosphere enriched with 5% $CO_2$.

The composition of example 3 is tested against the following allergens:
heavy metals (Al, As, Cd, Cr, Hg, Ni, Pb, Sr, Te)—ECP multi-element standard V Ref 0C467028 Merck;
tetramethylthiuram disulfide—T2 420;
2-mercaptobenzothiazole—M3301;
benzyl carbamate—B18200;
bisphenol—13302;
ethyl acrylate—W241806;
Araldite 506 epoxy resin—A3183;
hevein—latex 4335932;
methanol at 30% w/w—116 99031.

At $T_0$, the composition of example 3 above is applied to the skin explants at a dosage of 3 $mg/cm^2$. It is left to dry for 15 min. 25 µl of a solution of one of the allergens chosen from the above list are then applied to the skin explants protected by the emulsion of example 3 (test) and are also applied to nonprotected skin explants (nonprotected control). They are left to stand until $T_{4\,h}$, which represents 4 hours of exposure to the allergen without washing or abrasive friction.

In parallel, explants protected with the emulsion but which are not brought into contact with a test substance (control) are prepared in the same way.

The effectiveness of protection against allergens is measured by CD1a immunostaining analysis. First, paraffin sections of Langerhans cells are immunostained with anti-CD1a monoclonal antibodies (ref. IM1590, clone O10, Beckman Coulter) for 1 hour at ambient temperature. This immunostaining is reinforced with a streptavidin/biotin system (Vector, PK-7200) and revealed using VIP (Vector, SK-4600). The nuclei are counterstained with Masson's hemalum. The Langerhans cells are counted on each section along the epidermis. The length of each section is measured using the Olympus Cell software and the average number of Langerhans cells per centimeter of epidermis is calculated.

The effectiveness of protection against the allergen is measured by the number of Langerhans cells which have not migrated.

Samples are taken for all the explants at $T_0$ and at $T_{4\,h}$ and are photographed.

Figure 2:
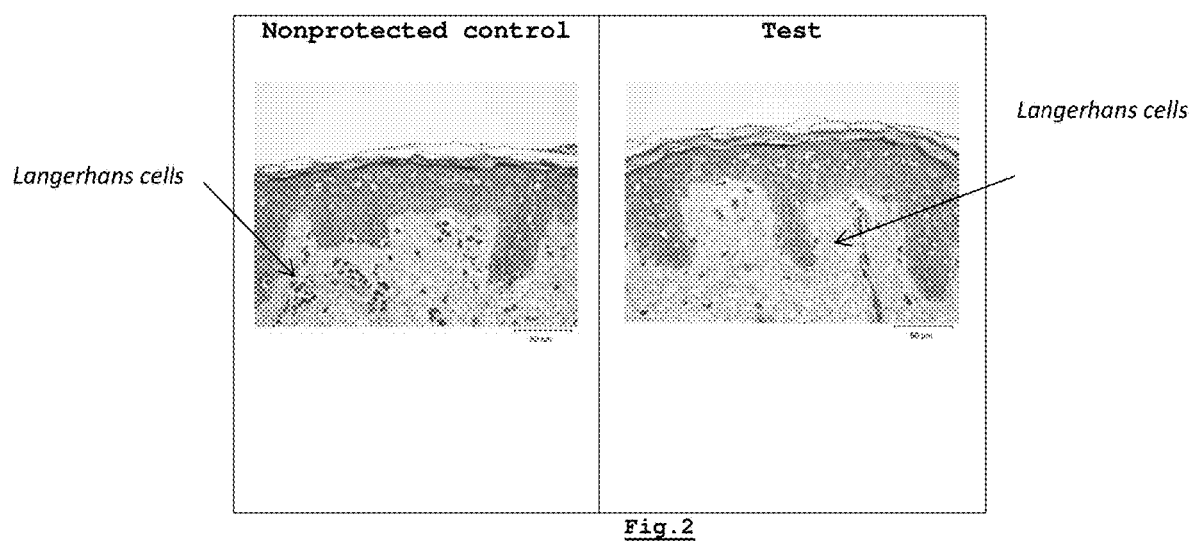
FIG. 2 is a photograph by Scanning Electron Microscopy of the explants of Example 4 at T=4 h.

The results are presented in FIGS. 1 and 2. FIG. 1 represents the explants at $T_0$ and FIG. 2 at $T_{4\,h}$ for hevein.

At $T_0$, the stratum corneum is thin, compact and moderately filled with keratin at the surface and notably at the bottom. The epidermis exhibits from 4 to 5 cell layers with good morphology and slight spongiosis on the stratum germinativum. The relief of the junction between the dermis and epidermis is marked. The papillary dermis exhibits quite thick fibers constructing a dense network and it is well-populated with cells, without any apparent histological lysis area.

The epidermis of the nonprotected explants exhibits 4-5 cell layers with notable morphological changes. These changes are characterized by a marked cytoplasmic denaturation (protein alteration), marked pyknosis and a marked spongiosis on the stratum germinativum.

On the other hand, the protected and "control" explants show no significant histological change.

Similar results were obtained with each of the other allergens tested.

The absence or the low level of cell change and also the low interleukin concentration demonstrated that the composition of example 3 effectively protects the skin against hevein.

Example 5: Composition for Condom 100 ml of lubricating gel comprising the following:
99 ml of purified water,
0.5 g of scleroglucan,
0.4 mg of amphoteric chelating agent,
are prepared in the following way.

This gel is applied by coating on the internal and external faces of a condom made of natural rubber in an amount of 2.0+/−0.5 $mg/cm^2$.

The invention claimed is:
1. A method of preventing a contact allergy selected from the group consisting of contact dermatitis, eczema, rhinitis, conjunctivitis, asthma attacks, anaphylactic shock and combinations thereof developed through repeated contact with rubber, said method comprising:

applying to the skin or mucous membrane of a patient sensitive to repeated contact with rubber and liable to develop said contact allergy an effective amount of at least one amphoteric chelating agent which is a complex based on aluminum and on ethylenediaminetetraacetic acid or the trisodium salt thereof, having the general formula $[Al(Y)B_n]^{c'}D_c$ with B being $OH^-$, $BO_2^-$ or $H^+$, Y being a tetracarboxylate which can be protonated four times so as to form ethylenediaminetetraacetic acid, n being an integer equal to 0, 1, 2 or 3, D being a counterion, c being an integer equal to 0, 1, 2 or 3, and c' being a relative number having the same absolute value as c, and being stabilized with an amino acid selected from the group consisting of histidine, arginine, phenylalanine, isoleucine, leucine, methionine, proline, valine, tryptophan, serine, glutamine, cystine, and mixtures thereof, and contacting with rubber the skin or mucous membrane to which the amphoteric chelating agent has been applied, wherein said effective amount of said at least one amphoteric chelating agent is applied to the skin or mucous membrane before contact between the rubber and the skin or mucous membrane, wherein said at least one amphoteric chelating agent provides a physical and chemical barrier against allergens, and wherein said effective amount of said at least one amphoteric chelating agent prevents said contact allergy selected from the group consisting of contact dermatitis, eczema, rhinitis, conjunctivitis, asthma attacks, anaphylactic shock, and combinations thereof from developing through repeated contact with rubber.

2. The method according to claim 1, wherein the amphoteric chelating agent is incorporated into a device and/or into a composition.

3. A device, comprising:

a part made of rubber, which is intended to come into contact with the skin or the mucous membranes, said contact capable of causing a contact allergy through repeated contact with said rubber, a surface of said part, which is intended to come into contact with the skin or the mucous membrane, being covered with a layer of a composition containing at least one amphoteric chelating agent which comprises a complex based on aluminum and on ethylenediaminetetraacetic acid or the trisodium salt thereof, having the general formula $[Al(Y)B_n]^{c'}D_c$ with B being $OH^-$, $BO_2^-$ or $H^+$, Y being a tetracarboxylate which can be protonated four times so as to form ethylenediaminetetraacetic acid, n being an integer equal to 0, 1, 2 or 3, D being a counterion, c being an integer equal to 0, 1, 2 or 3, and c' being a relative number having the same absolute value as c, and being stabilized with an amino acid selected from the group consisting of histidine, arginine, phenylalanine, isoleucine, leucine, methionine, proline, valine, tryptophan, serine, glutamine, cystine, and mixtures thereof, wherein the surface of said part is covered by the composition in amount of 0.5 to 5 mg/cm² of the surface of said part, and wherein the contact allergy developed through repeated contact with said rubber is selected from the group consisting of contact dermatitis, eczema, rhinitis, conjunctivitis, asthma attacks, anaphylactic shock and combinations thereof.

4. The device according to claim 3, chosen from condoms, gloves, finger stalls, bandages, compresses, and medical devices.

5. The device according to claim 3, wherein the layer in which the amphoteric chelating agent is present is a film deposited at least on the surface intended to come into contact with the skin and/or the mucous membranes.

6. A method of preventing a contact allergy selected from the group consisting of contact dermatitis, eczema, rhinitis, conjunctivitis, asthma attacks, anaphylactic shock and combinations thereof developed through repeated contact with rubber, said method comprising:

applying to the skin or mucous membrane of a patient sensitive to repeated contact with rubber and liable to develop said contact allergy, a composition comprising:

at least one excipient, and from 0.01% to 5%, by weight of the composition, of at least one amphoteric chelating agent which is a complex based on aluminum and on ethylenediaminetetraacetic acid or the trisodium salt thereof, having the general formula $[Al(Y)B_n]^{c'}D_c$ with B being $OH^-$, $BO_2^-$ or $H^+$, Y being a tetracarboxylate which can be protonated four times so as to form ethylenediaminetetraacetic acid, n being an integer equal to 0, 1, 2 or 3, D being a counterion, c being an integer equal to 0, 1, 2 or 3, and c' being a relative number having the same absolute value as c;

and stabilized with an amino acid selected from the group consisting of histidine, arginine, phenylalanine, isoleucine, leucine, methionine, proline, valine, tryptophan, serine, glutamine, cystine, and mixtures thereof, and contacting with rubber the skin or mucous membrane to which the composition has been applied, wherein the composition is applied to the skin or mucous membrane before contact between the rubber and the skin or mucous membrane, wherein said at least one amphoteric chelating agent provides a physical and chemical barrier against allergens, and wherein said 0.01% to 5%, by weight of the composition, of said at least one amphoteric chelating agent is an effective amount for preventing said contact allergy selected from the group consisting of contact dermatitis, eczema, rhinitis, conjunctivitis, asthma attacks, anaphylactic shock and combinations thereof developed through repeated contact with rubber.

7. The method according to claim 6, wherein said at least one excipient is selected from the group consisting of a gelling agent, surfactants, synthetic or natural waxes, synthetic or natural oils, moisturizing agents and emollients, antiperspirants, texture-improving additives, and mixtures thereof.

8. The method according to claim 6, wherein the at least one excipient is a gelling agent selected from the group consisting of hydrophilic gelling agents, and silicon gelling agents.

9. The method according to claim 7, wherein the composition is a lubricating preparation chosen from a hydrophilic lubricating preparation, a silicone lubricating preparation or a vaseline-based lubricating preparation.

10. The device according to claim 4, wherein the layer in which the amphoteric chelating agent is present is a film deposited at least on a surface intended to come into contact with the skin and/or the mucous membranes.

11. A method of preventing a contact allergy developed through repeated contact with an allergen selected from the group consisting of latex proteins, tetramethylthiuram disulfide, 2-mercaptobenzothiazole, benzyl carbamate, bisphenol, ethyl acrylate, araldite 506 epoxy resin, methanal, protein-type allergens, and mixtures thereof, said method comprising:

applying to the skin or mucous membrane of a patient sensitive to repeated contact with said allergen and liable to develop said contact allergy, a composition comprising from 0.01% to 5%, by weight of the composition, of at least one amphoteric chelating agent which comprises a complex based on aluminum and on ethylenediaminetetraacetic acid or the trisodium salt thereof, the agent having the general formula $[Al(Y)B_n]^c D_c$ with B being $OH^-$, $BO_2^-$ or $H^+$, Y being a tetracarboxylate which can be protonated four times so as to form ethylenediaminetetraacetic acid, n being an integer equal to 0, 1, 2 or 3, D being a counterion, c being an integer equal to 0, 1, 2 or 3, and c' being a relative number having the same absolute value as c, wherein the amphoteric chelating agent is stabilized with an amino acid selected from the group consisting of histidine, arginine, phenylalanine, isoleucine, leucine, methionine, proline, valine, tryptophan, serine, glutamine, cystine, and mixtures thereof, and contacting with said allergen the skin or mucous membrane to which the composition has been applied, wherein the composition applied to the skin or mucous membrane before contact between said allergen and the skin or mucous membrane, wherein said at least one amphoteric chelating agent provides a physical and chemical barrier against said allergen, and wherein said 0.01% to 5%, by weight of the composition, of said at least one amphoteric chelating agent is an effective amount for preventing said contact allergy when the patient is repeatedly in contact with said allergen selected from the group consisting of latex proteins, tetramethylthiuram disulfide, 2-mercaptobenzothiazole, benzyl carbamate, bisphenol, ethyl acrylate, araldite 506 epoxy resin, methanal, protein-type allergens, and mixtures thereof, and the protein-type allergen being selected from the group consisting of profilins, tropomyosins, lipid transfer proteins (LTPs), PR-10 bet V1-like proteins, polcalcins, beta-parvalbumins, 2s albumins, beta-expansins, polygalacturonases, Antigen 5 (Ag5), albumins, caseins, lipocalins, grass group 5 allergens, 11s globulins, 7s vicilin-like globulins, grass group 4 allergens, papain-like cysteine proteases, serine protease inhibitors, class 1 chitinases and thaumatin-like proteins.

12. A method of preventing a contact allergy developed through repeated contact with rubber, said method comprising:

applying to the skin or mucous membrane of a patient sensitive to repeated contact with rubber and liable to develop said contact allergy, a composition comprising:

from 0.01% to 5%, by weight of the composition, at least one amphoteric chelating agent which comprises a complex based on aluminum and on ethylenediaminetetraacetic acid or the trisodium salt thereof, having the general formula $[Al(Y)B_n]^c D_c$ with B being $OH^-$, $BO_2^-$ or $H^+$, Y being a tetracarboxylate which can be protonated four times so as to form ethylenediaminetetraacetic acid, n being an integer equal to 0, 1, 2 or 3, D being a counterion, c being an integer equal to 0, 1, 2 or 3, and c' being a relative number having the same absolute value as c;

and at least one gelling agent, wherein the amphoteric chelating agent is stabilized with an amino acid selected from the group consisting of histidine, arginine, phenylalanine, isoleucine, leucine, methionine, proline, valine, tryptophan, serine, glutamine, cystine, and mixtures thereof, and wherein the gelling agent is selected from the group consisting of hydrophilic gelling agents and silicone gelling agents, and contacting with rubber the skin or mucous membrane to which the composition has been applied, wherein the composition is applied to the skin or mucous membrane before contact between the rubber and the skin or mucous membrane, wherein said at least one amphoteric chelating agent provides a physical and chemical barrier against allergens, and wherein said 0.01% to 5%, by weight of the composition, of said at least one amphoteric chelating agent is an effective amount for preventing contact allergy when the patient is repeatedly in contact with rubber.

13. The device according to claim 3, wherein the device is a medical device selected from the group consisting of catheters, tubing, draining devices, perfusion devices, medical devices for use in urology, and medical devices for respiratory access.

14. The method according to claim 6, wherein said at least one excipient is a texture-improving additive selected from the group consisting of conditioners, preservatives, cosmetic and food dyes, fragrances, flavorings, and pH-regulating agents.

15. The method according to claim 8, wherein the silicone gelling agent is a polysiloxane.

16. The method according to claim 6, wherein the at least one excipient is a hydrophilic gelling agent selected from the group consisting of acrylic acid polymers and copolymers, C10-C30 alkyl acrylate/acrylate crosslinked polymers, polyacrylamide, poloxamer, cellulose-based derivatives, silicas, silicates, magnesium aluminum silicates, chitin and derivatives thereof, gelatin, xanthan, dextran, gellan, carraghenans, alginates, agar, pectin, acacia gum, karaya gum, tragacanth, gum arabic, guar gum, locust bean gum, starch and derivatives thereof and scleroglucan.

17. The method according to claim 16, wherein cellulose-based derivatives are esters and ethers.

18. The method according to claim 1, wherein B is $BO_2^-$ in the general formula of the complex.

19. The device according to claim 3, wherein B is $BO_2^-$ in the general formula of the complex.

20. The method according to claim 6, wherein B is $BO_2^-$ in the general formula of the complex.

21. The method according to claim 11, wherein B is $BO_2^-$ in the general formula of the complex.

22. The method according to claim 12, wherein B is $BO_2^-$ in the general formula of the complex.

* * * * *